(12) United States Patent
Cappello

(10) Patent No.: US 9,155,755 B2
(45) Date of Patent: Oct. 13, 2015

(54) DIETARY SUPPLEMENTS INCLUDING GLUCAN AND FULVIC ACID

(71) Applicant: Cappellos, Inc., King of Prussia, PA (US)

(72) Inventor: John V. Cappello, King of Prussia, PA (US)

(*) Notice: Subject to any disclaimer, the term of this patent is extended or adjusted under 35 U.S.C. 154(b) by 0 days.

(21) Appl. No.: 14/207,050

(22) Filed: Mar. 12, 2014

(65) Prior Publication Data

US 2014/0271558 A1 Sep. 18, 2014

Related U.S. Application Data

(60) Provisional application No. 61/798,283, filed on Mar. 15, 2013.

(51) Int. Cl.

| | |
|---|---|
| *A61K 31/593* | (2006.01) |
| *A61K 31/375* | (2006.01) |
| *A61K 31/194* | (2006.01) |
| *A61K 31/137* | (2006.01) |
| *A61K 35/74* | (2015.01) |
| *A61K 38/00* | (2006.01) |
| *A61K 31/366* | (2006.01) |
| *A61K 36/73* | (2006.01) |
| *A61K 45/06* | (2006.01) |
| *A61K 31/716* | (2006.01) |
| *A61K 35/748* | (2015.01) |
| *A61K 31/536* | (2006.01) |
| *A23L 1/00* | (2006.01) |
| *A61K 36/481* | (2006.01) |

(52) U.S. Cl.
CPC ............. *A61K 31/716* (2013.01); *A23L 1/00* (2013.01); *A61K 31/137* (2013.01); *A61K 31/194* (2013.01); *A61K 31/366* (2013.01); *A61K 31/375* (2013.01); *A61K 31/536* (2013.01); *A61K 31/593* (2013.01); *A61K 35/748* (2013.01); *A61K 36/481* (2013.01); *A61K 36/73* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2004/0161435 | A1* | 8/2004 | Gupta | ............................ 424/401 |
| 2011/0262505 | A1* | 10/2011 | Athwal | ......................... 424/401 |

OTHER PUBLICATIONS

Beattie, Anne; et al; "Studies on the Metabolism of the Chrysophyceae: Comparative Structural Investigations on Leucosin (Chrysolaminarin) Separated from Diatoms and Laminarin from Brown Algae" Biochemical Journal, 79, 531-537, 1961.*

Troxler, Robert F; et al; "The alpha and beta Subunits of Cyanidium caldarium Phycocyanin: Properties and Amino Acid Sequences at the Amino Terminus" Biochemistry, 14, 268-274, 1975.*

Radwan, Amal; et al; "Isolation of humic acid from the brown algae Ascophyllum nodosum, Fucus vesiculosus, Laminaria saccharina and the marine angiosperm Zostera marina" Journal of Applied Phycology, 8, 553-562, 1997.*

Carder, Kendall L; et al; "Marine humic and fulvic acids: Their effects on remote sensing of ocean chlorophyll" Limnology and Oceanography, 34, 68-81, 1989.*

Ravindra, Anupama P; "Value-added food: Single cell protein" Biotechnology Advances, 18, 459-479, 2000.*

Stoner, Gary D; et al; "Pharmacokinetics of Anthocyanins and Ellagic Acid in Healthy Volunteers Fed Freeze-Dried Black Raspberries Daily for 7 Days" Journal of Clinical Pharmacology, 45, 1153-1164, 2004.*

* cited by examiner

*Primary Examiner* — Blaine Lankford, Jr.
*Assistant Examiner* — David Berke-Schlessel
(74) *Attorney, Agent, or Firm* — Lawrence J. Shurupoff

(57) ABSTRACT

Beta glucan and fulvic acid can be combined in a dietary supplement as a partial substitute or complete replacement for blue green algae and/or brown seaweed and its derivatives. Beta glucans are widely available as derivatives of Brewer's yeast and fulvic acid is widely available as well. These supplements are not subject to the vagaries of weather-influence growing seasons as is the case with blue green algae and brown seaweed. When combined, beta glucan and fulvic acid can provide a less costly dietary supplement than blue green algae and brown seaweed and its derivatives such as fucoidan.

10 Claims, No Drawings

DIETARY SUPPLEMENTS INCLUDING GLUCAN AND FULVIC ACID

FIELD OF DISCLOSURE

The present disclosure relates to dietary and nutritional supplements and life-enhancing compositions which can be administered orally to promote stem cell production and overall wellness. A combination of readily available and cost effective ingredients has been found to be a viable substitute for more expensive stem cell stimulators such as blue-green algae and fucoidan derived from brown algae and brown seaweed.

BACKGROUND AND SUMMARY

Recent attention has been directed to naturally stimulating the human body to produce stem cells. Stem cells not only combat disease, they also contribute to health maintenance and reduce the effects of injury and aging. Dietary supplements containing blue-green algae can aid in the body's natural production of stem cells as well as provide the essential vitamins, minerals, proteins and nutrients required to support life. One form of blue-green algae known as Aphanizomenon flos-aqua (AFA) is particularly effective in stimulating natural stem cell production within the body while also providing the vitamins, minerals, proteins and nutrients required to support life.

Some dietary supplements combine AFA with supplemental phycocyanin to reduce or prevent inflammation caused by injury, arthritis and/or irritants. Phycocyanin can be extracted directly from AFA and provided in the form of a concentrated supplement to AFA. Alternatively, phycocyanin can be provided in the less costly form of *Arthrospira platentis* (AP) which contains about 19% to 20% by weight of phycocyanin.

Another supplement that has been added to AFA is phenylethylamine (PEA) such as in the form of PEA hydrochloride. PEA has been found, when combined with AFA, to reduce depression and increase or promote alertness.

Stem cell production can also be naturally enhanced within the human body by ingesting certain brown algae and/or brown seaweed. In particular, a brown algae derivative called fucoidan has been found to promote stem cell production and can be taken alone or in combination with AFA. A benefit of fucoidan is that it contains about 60% by weight of desirable polysaccharides while AFA contains about 20% by weight of polysaccharides. Accordingly, fucoidan, when ingested, provides more polysaccharides per unit weight than AFA allowing for smaller dosages while providing the same amount of polysaccharides as larger dosages of relatively expensive AFA.

Unfortunately, the availability of both AFA and fucoidan is limited and variable. There are a very limited number of suppliers of AFA and fucoidan, and as the popularity and demand for these dietary supplements has increased in recent times, the cost of AFA and fucoidan has likewise risen. Moreover, the supply of these supplements is subject to the amount of AFA and fucoidan that can be harvested from season to season. This combination of factors makes it difficult to provide a consistent supply of dietary supplements containing AFA and/or fucoidan to the marketplace.

Accordingly, it would be desirable to find a more readily available dietary supplement for enhancing stem cell production and promoting health. It would also be desirable to find a less costly dietary substitute or combination of dietary substitutes for AFA and/or fucoidan and other supplements which are known to stimulate stem cell growth when ingested as a dietary supplement.

SUMMARY

In order to avoid the problems of the high costs and limited and undependable supplies of AFA and fucoidan, dietary formulations have been developed in accordance with this disclosure that can not only naturally stimulate stem cell production but also provide virtually all the vitamins, minerals and nutrients provided by AFA and/or fucoidan. These formulations can either supplement or totally replace AFA and/or fucoidan in any dietary supplement previously dependent on AFA and fucoidan.

In accordance with this disclosure, improved dietary supplements have been developed that contain one or more ingredients that can increase the production of human stem cells when ingested, while providing additional health benefits associated with high concentrations of polysaccharides. Additional benefits can be derived by adding AP to a dietary supplement to provide phycocyanin and other amino acids found in AP. As disclosed below, a viable substitute for the trace minerals and amino acids found in AFA and fucoidan has also been identified.

It has be discovered that the combination of beta glucan and fulvic acid can serve as a viable addition to or substitute for AFA and/or fucoidan without the drawbacks of limited supply, undependable and inconsistent supply and high cost. That is, both beta glucan and fulvic acid are not dependent upon growing seasons with variable harvests. They are commonly available commercially in dependable and consistent supply from many sources at relative low cost as compared to AFA.

An added benefit of beta glucan, and in particular, an isomer of beta glucan called beta-1,3/1,6 glucan, is that it includes a greater amount per unit weight of polysaccharides than AFA. As discussed in U.S. Pat. No. 7,473,427, polysaccharides aid in the transport of dietary supplements including phenylethylamine (PEA) and phycocyanin through the digestive tract and into the bloodstream. This is important not only from a simple efficiency perspective, but also from an economic perspective, as PEA and phycocyanin are quite expensive. PEA is a desirable dietary supplement and can be provided in the form of phenylethylamine hydrochloride to reduce depression and promote alertness. Phycocyanin is a desirable dietary supplement for reducing inflammation caused by injury, arthritis or irritants. Both PEA and phycocyanin are found in AFA.

Fulvic acid replaces the minerals and amino acids otherwise provided by AFA and can provide those minerals in a more bioavailable form. The combination of beta glucan and fulvic acid results in a greater utilization of all of the active components of AP to provide a more efficient and effective dietary supplement than that provided by AFA alone.

DESCRIPTION OF REPRESENTATIVE EMBODIMENTS

It has been found that beta-glucans, particularly those isomers of beta glucan having D-glucose units with (1,3) links and with side-chains of D-glucose attached at the (1,6) position can provide the stem cell enhancing benefits of AFA and fucoidan, but at a lower cost, with greater availability and without the problems associated with variable growing seasons. These beta-glucans are referred to as beta-1,3/6, glucan. It has been found that beta-1,3/1,6 glucan can, when ingested, increase the amount of progenitor and adult stem cells in circulation while providing additional health benefits. Of course, any isomer of beta glucan can provide similar benefits. As used herein, the term beta glucan includes all isomers of beta glucan.

Beta-glucan can be obtained from the cell wall of brewer's yeast, also known as Saccharomyces cerevisiae and from other sources, such as bran. Beta-glucan is available from many commercial sources without dependence upon algae and seaweed crop performance which is subject to the vagaries of the weather and other factors which can affect plant growth in lakes and oceans. Beta-glucan eliminates the uncertainties of growing algae and seaweed in good and bad growing conditions.

A particularly beneficial aspect of beta-glucan is that it contains 100% polysaccharides. Polysaccharides benefit and enhance the body's utilization of the beneficial or key ingredients of AP and other supplements through a more efficient transport of ingredients into the bloodstream. Because of this increased efficiency, lesser amounts of ingredients need be ingested in order to achieve the same amount of ingredients circulating in the bloodstream as compared to supplements without beta-glucan due to the greater amount of polysaccharides provided by beta-glucan.

While beta-glucan can supplement or replace in whole or in part AFA, as well as fucoidan and/or any other stem cell promoting supplement in any dietary formulation intended to increase adult stem cells and other progenitor cells, it would be desirable to supplement and provide the trace vitamins and nutrients provided by AFA and/or fucoidan when substituting beta-glucan for AFA and/or fucoidan. One solution to this lower amount of vitamins and nutrients in beta glucan than AFA is the discovery that fulvic acid derived from humic acid can provide as much or more of the trace minerals as well as many of the amino acids provided by AFA and/or fucoidan.

Humic and fulvic acids (fulvic acids are humic acids of lower molecular weight and higher oxygen content than other humic acids) are commonly used as soil supplements in agriculture and can also be used as a human nutritional supplement. As a nutritional supplement, fulvic acid can be found in liquid and solid forms as a component of mineral colloids. Fulvic acids are polyelectrolytes and are unique in that they diffuse easily through membranes whereas many other colloids do not do so in the same way.

Fulvic acid product is consistently and widely available commercially. A mineral and trace mineral profile from a laboratory scan identified seventy four mineral analytes in fulvic acid. An amino acid profile for fulvic acid identified eighteen amino acids present in fulvic acid. This combination of minerals and amino acids provides an effective supplement when combined with beta-glucan that in combination closely matches the minerals and amino acids found in AFA and fucoidan.

That is, a combination of beta-glucan and fulvic acid provides similar and potentially better stem cell enhancement and health benefits than AFA and fucoidan. The combination of beta-glucan and fulvic acid can readily replace AFA and fucoidan in whole or in part at lower cost and due at least in part to greater amounts of polysaccharides, improve upon the effectiveness of prior dietary formulations that relied on AFA and/or fucoidan.

One example of a dietary supplement formulated in accordance with this disclosure includes the following dosages of ingredients suitable for ingestion as a single capsule or tablet: from at least about 30 mg to about 220 mg and preferably about 125 mg of beta glucan, preferably beta-1,3/1,6 glucan;

from at least about 25 mg to about 175 mg and preferably about 100 mg of fulvic acid;

from at least about 25 mg to about 175 mg and preferably about 100 mg of phycocyanin, and preferably provided in the form of about 125 mg to about 875 mg and preferably about 175 mg of *Arthrospira platentis*; and from at least about 6 mg to about 45 mg and preferably about 25 mg of phenylethylamine (PEA). This formulation can be provided in the form of one capsule or tablet taken twice daily.

The *Arthrospira platensis* in the formulations disclosed herein can be supplemented or replaced with pure phycocyanin extract, such as derived from AFA. About 95 mg of pure phycocyanin can replace the 500 mg of *Arthrospira platensis* in the example above. As referred to hereafter, the combination of beta glucan, fulvic acid and phycocyanin is called a base formulation or base composition and the addition of PEA to the base formulation or base composition is called a primary formulation or primary composition.

The combination of beta glucan, such as beta-1,3/1,6 glucan, fulvic acid, and phycocyanin can serve as a base formulation, such as in the amounts set forth in the example above. This base formulation or base composition provides an effective dietary supplement for stimulating stem cell production and enhancing health. The base formulation can be combined with PEA and/or the minimum daily requirement of vitamins and/or minerals for even greater health benefits.

A daily dosage of the base formulation includes at least about 60 mg to about 440 mg or more of beta glucan and any isomers thereof. A preferred daily dosage of beta glucan is at least about 100 mg to about 300 mg of beta glucan and any isomers thereof. A more preferred daily dosage of beta glucan and any isomers thereof is at least about 150 mg to about 250 mg. Each of these dosages can be taken orally in the form of one or preferably two or more tablets or capsules. As used throughout herein, the term "about" mean plus or minus 15%.

A daily dosage of the base formulation further includes at least about 50 mg to 350 mg or more of fulvic acid. A preferred daily dosage of fulvic acid is at least about 100 mg to about 200 mg of fulvic acid. A more preferred daily dosage of fulvic acid is at least about 125 mg to about 175 mg. Each of these dosages can be taken orally in the form of one or preferably two or more tablets or capsules.

A daily dosage of the base formulation also includes at least about 50 mg to about 350 mg of phycocyanin (250 to 1750 mg of AP). Phycocyanin can be provided as *Arthrospira platensis* (AP) at about five times the weight of pure phycocyanin. A preferred daily dosage of phycocyanin includes at least about 150 mg to about 250 mg of phycocyanin (750 to 1250 mg of AP). A more preferred daily dosage of phycocyanin includes at least about 175 mg to 225 mg of phycocyanin (875 to 1225 mg AP). Each of these dosages can be taken orally in the form of one or preferably two or more tablets or capsules.

The three ingredients of the base formulation, namely, beta glucan, fulvic acid and phycocyanin can be combined, and provided as a capsule or tablet. To facilitate ingestion, the daily dosages of the base formulation can be provided as two or more easily swallowed tablets or capsules taken once or twice daily.

As noted above, the base formulation can be supplemented with a daily dosage of at least about 12 mg to 90 mg of PEA. A preferable daily dosage is at least about 20 mg to about 40 mg of PEA for reducing depression and increasing alertness.

While the combination of beta glucan, fulvic acid, and phycocyanin provides an effective base composition, and with the addition of PEA, an effective primary composition for stimulating stem cell production, the ingredients in the base and primary compositions can be made more effective in stimulating and nourishing stem cell production with the addition of one or more of the ingredients disclosed below. That is, it has been found that by supplementing the base or primary compositions with one or more additional ingredients the amount of stem cell production, body repair and the degree of anti-aging can be significantly improved. The result is a life-extending dietary supplement that not only retards the aging process but also repairs prior damage to existing cells.

By adding vitamins and/or minerals to the base or primary compositions, greater health benefits can be achieved. For example, vitamin D3 is a potent inhibitor of the inflammatory response and has been associated with increased stem cell circulation. Vitamin D3 also can improve adult stem cell circulation. Adding vitamin D3 to the base or primary compositions alone or in combination with other vitamins or minerals stimulates the activation of dormant adult stem cells in the bone marrow, leading to improved stem cell production. While the minimum daily requirement of 400 IU of vitamin D3 is standard or common, 250 IU to 5000 IU (6.25 mcg to 125 mcg) of vitamin D3 and preferably 1000 to 2000 IU (25 mcg to 50 mcg) of vitamin D3 can be taken in combination with the base composition, alone or with one or more of the other ingredients disclosed herein.

Vitamin C can be added to the base composition alone or in combination with one or more of the ingredients disclosed herein. As noted above, vitamin C increases the differentiating abilities of adult stem cells. Vitamin C can be added to the base and primary compositions in the amount of 15 mg to 90 mg or more per dosage.

The base and primary compositions can be combined with one or more additional vitamins and/or minerals to further promote health and longevity. By combining the base and primary compositions in the amounts and ranges as set forth herein, one can increase one's health and longevity significantly.

For example, by adding one or more, all, or any combination of the following vitamins and minerals to the base or primary formulations, a life enhancing result can be achieved over and above that provided by the base and primary compositions. Supplemental vitamins include vitamin A (5000 IU), vitamin D3 (1000 IU), vitamin C (90 mg), vitamin E (30 IU), vitamin K (40 mcg), vitamin B1 (2.3 mg), vitamin B2 (2.6 mg), niacin (20 mg), folic acid (400 mcg), and vitamin B12 (9 mcg). Supplemental minerals include calcium (200 mg), biotin (300 mcg), pantothentic acid (10 mg), iron (6 mg), phosphorous (45 mg), iodine (150 mcg), magnesium (100 mg), zinc (15 mg), selenium (70 mcg), copper (2 mg), manganese (2 mg), chromium (120 mcg), and molybdenum (75 mcg).

The blend of vitamins and minerals listed above can be advantageously combined with the base and primary compositions. The resulting aggregate dietary composition can be provided in the form of two 900 mg pills or tablets to be taken orally at least once a day and potentially twice a day. While the amounts listed above provide effective results, each amount can be reduced by as much as 50% or increased by as much as 200%, 300% or more for even more effective results. The vitamins and minerals listed above, when added to the base or primary compositions, provides a daily vitamin and mineral formulation with complete stem cell nutrition support.

While the combination of beta glucan, fulvic acid, PEA and phycocyanin provides an effective primary composition for stimulating stem cell production, the ingredients in this primary composition can be made more effective in stimulating stem cell production with the addition of one or more of the ingredients disclosed below. That is, it has been found that by supplementing this primary composition with one or more additional ingredients, the amount of stem cell production and the degree of anti-aging can be significantly improved. The result is a life-extending dietary supplement that not only retards the aging process but also repairs prior damage to existing cells.

Anti-aging and body repair can be improved by adding the anti-oxidant curcumin to the base composition and to the primary composition of beta glucan, fulvic acid, PEA and phycocyanin. Curcumin contains high levels of polyphenols and is available as a 95% standardized extract of *curcuma longa* also known as the spice turmeric, a member of the ginger root family. Curcumin can be added to either the base composition or the primary composition alone, or with one or more of the additional ingredients identified below.

Curcumin is the principal curcuminoid of turmeric. Fifty milligrams of 95% standardized curcumin extract provides the equivalent amount of curcuminoids obtained by eating up to two grams of the spice turmeric. Health and anti-aging benefits are associated with curcumin. Studies have been conducted regarding a link between curcumin and mTOR (mammalian target of rapamycin) inhibition. The inhibition of mTOR is beneficial as it limits a tumor's ability to grow and spread.

Another beneficial additive is silymarin, which works to stabilize liver cell membranes and acts as an antioxidant to protect liver cells from free radical damage. Added to the base or primary composition of whole blue-green algae, PEA and phycocyanin, alone or with one or more of the other additives discussed herein, silymarin helps to regenerate healthy liver cells.

Another anti-aging ingredient is resveratrol, available as a 98% trans isomer. Resveratrol is believed to activate the SIRT-1 anti-aging gene and enhance the beneficial anti-aging effects of the primary composition when added to the base or primary composition singularly or in combination with any one or more of the other additives described herein.

Astragalus root includes a chemical that prevents or slows progressive telomere shortening, reduces DNA damage and assists in the ability to repair DNA. Moreover, astragalus root typically includes about 20% by weight of polysaccharides which possess an additional anti-aging effect related to the anti-oxidative properties of polysaccharides. In addition, the polysaccharides in astragalus act as a transport medium for astragoloside IV, thereby increasing its beneficial effect.

Another effective anti-aging ingredient is astragoloside IV which is believed to be a telomerase activator. It is a component of astragalus known to repair bits of telomeres. By activating the enzyme telomerase, the short bits of DNA forming telomeres can be replaced. Astragoloside IV can be added to the primary composition alone or in combination with one or more of the other ingredients disclosed herein.

Still another anti-aging ingredient is L-carnosine, a naturally occurring dipeptide, which can oppose age-related glycolation. L-carnosine also appears to reduce the rate at which telomeres shorten and delay replicative cellular senescence and extend the lifespan of human cells. Added alone or with any one or more of the other ingredients to the base and primary compositions, L-carnosine provides beneficial anti-aging properties.

The length of telomeres on leukocytes or "white blood cells" (LTL) is a predictor of age-related diseases. The length of these telomeres decreases with cell division and with increased inflammation. Vitamin D3 is a potent inhibitor of the inflammatory response and reduces the turnover of leukocytes. Studies have associated higher serum vitamin D3 levels with lower telomeric aging and increased stem cell circulation. Adding vitamin D3 to the base and primary composition alone or in combination with one or more of the other ingredients disclosed herein preserves LTL and thereby slows aging. Vitamin D3 can enhance both telomere length and improve adult stem cell circulation. Vitamin D3 also stimulates the activation of dormant adult stem cells in the bone marrow, leading to improved stem cell production. While the minimum daily requirement (MDR) of 400 IU of vitamin D3 is standard or common, 250 IU to 5000 IU (6.25 mcg to 125 mcg) of vitamin D3 and preferably 250 to 2000 IU (6.25 mcg to 50 mcg) of vitamin D3 can be taken in combination with the primary or base formulations, alone or with any one or more of the other ingredients disclosed herein.

Vitamin C can be added to the base or primary formulations alone or in combination with one or more of the other ingredients disclosed herein. Vitamin C increases the differentiating abilities of adult stem cells. Vitamin C can be added to the base and primary formulations in the amount of 15 mg to 60 mg per dosage.

Trimethylglycine (TMG) in an anhydrous form increases absorption from the digestive tract into the bloodstream of most dietary supplements including those disclosed herein. Trimethylglycine also functions as a methyl donor. Adding 0.5 to 15 mg of TMG to the primary composition alone or with any other ingredient disclosed herein increases the effectiveness and efficiency of the formulations.

Example

One representative anti-aging formulation of a beneficial dietary supplement for enhancing stem cell formation, slowing the aging process and repairing damaged cells includes:
125 mg of beta glucan (B-1,3/6 glucan);
75 mg of fulvic acid;
170 mg of *arthrospira platentis* containing 19% to 20% phycocyanin, or an equivalent amount of phycocyanin extract (e.g. up to 25 mg or more);
50 mg of curcumin (in the form of 95% standardized extract);
50 mg silymarin;
50 mg resveratrol;
50 mg astragalus root extract (20% polysaccharides);
50 mg astragoloside IV;
50 mg L-carnosine;
30 mg Vitamin C;
25 mg phenylethylamine;
25 mg anhydrous trimethylglycine (optional); and
500 IU (12.5 mcg) Vitamin D3;

The above composition can be provided in a 750 mg or larger tablet or gelatin capsule. The amount of each ingredient can vary widely within the ranges noted below.

Beta glucan—30 mg to 220 mg; fulvic acid 25 mg to 175 mg; phycocyanin—25 mg to 100 mg extract or 125 mg to 500 mg of *arthrospira platentis* at 19% to 20% by weight of phycocyanin; curcumin—95% standardized extract—5 mg to 150 mg; silymarin—5 mg to 150 mg; resveratrol (98%)—5 mg to 150 mg;
astragoloside IV—5 mg to 150 mg; L-carnosine—5 mg to 150 mg; phenylethylamine—2.5 mg to 75 mg; anhydrous trimethylglycine—0.5 mg to 15 mg. This formulation can be further enhanced with the addition of 250 to 5000 IU (6.25 mcg to 125 mcg) of Vitamin D3 and 15 to 60 mg of vitamin C.

While there are some formulations available for increasing stem cell production and others for telomere and genetic modifications, none is known which does both as described herein. The multiple-action formulation disclosed herein may be provided in a capsule, as a tablet or liquid for daily introduction into the human digestive tract. When provided in the 750 mg capsules or 900 mg tablets described above, two capsules or tablets can be taken daily, such as one capsule in the morning and one capsule in the evening. However, at least one capsule should be taken daily to achieve the results described above.

It should be noted that each of the ingredients in the formulation set forth immediately above serves to retard aging or to enhance the anti-aging effect of one or more of the other ingredients. Any combination of the base formulation of beta glucan, fulvic acid and phycocyanin or the primary formulation of beta glucan, fulvic acid, PEA and phycocyanin with one of more of the ingredients listed above can provide an anti-aging effect to promote body repair.

The combination of beta glucan, fulvic acid, and phycocyanin (such as in the form of *Arthrospira platentis*) and optionally phenylethylamine (PEA) provides a base or optional primary composition that promotes the human body's production of new stem cells. The remaining ingredients facilitate and enhance the repair and remediation of both new and old (existing) cells, and in particular, adult stem cells.

The efficacy of the base and primary formulations is improved by the addition of any one or more of the additional ingredient listed in 750 mg composition identified above. New stem cells with a full complement of telomeres are produced by the base and primary compositions and are protected against telomere shortening by any one or more of the remaining ingredients. These remaining ingredients also slow down the shortening of telomeres on existing cells so as to slow down the aging process.

Another supplement to the base or primary formulations that promotes the human body's production of new stem cells is the addition of 150 mg to 250 mg. of Saccharomyces cerevisiae, the scientific name for Brewer's yeast. Such an addition whether in capsule, tablet, solution or suspension would provide much needed trace RNA and DNA to the consumer for added potential anti-aging effect.

Another representative example of a dietary supplement formulated in accordance with this disclosure is: *arthrospira platensis* (450 mg), beta glucan (B-1,3/1,6 glucan) (125 mg), fulvic acid (75 mg), vitamin C (30 mg), AFA (30 mg), trimethlglycine (25 mg), PEA (15 mg), vitamin D (500 IU). This supplement can be taken twice daily as two 750 mg capsules such as vegicaps.

The base formulation of beta glucan, fulvic acid and phycocyanin and the primary formulation of beta glucan, fulvic acid, phycocyanin and phenylethylamine can be combined in the amounts noted above with a source of ellagic acid, such as any of the known sources of ellagitannins, to provide a strong antioxidant with cancer fighting properties. For example, 10 grams of black raspberry seed powder containing 16.65 mg/gram of total ellagic acid provides about 166.5 mg of endogenous ellagic acid per serving. Other food sources of ellagic acid include red raspberries, black raspberries, strawberries, cranberries, grapes, blackberries, blueberries, cherries, pomegranates and pomegranate juice. Apples also offer some ellagic acid. Other plant sources of ellagic acid include nuts. Varieties of nuts that offer appreciable amounts of ellagic acid include walnuts and pecans.

Additional health benefits can be achieved, as noted above, by combining the base or primary compositions with a source of ellagic acid and with one or more vitamins and/or one or more minerals as disclosed above. Adding from about 6.25 to 125 mg of vitamin D3 to the base or primary formulations disclosed above improves stem cell circulation within the human body.

Moreover, by adding from at least about 15 mg to several grams of vitamin C to the base or primary formulations disclosed above, the ability of stem cells to differentiate within the human body is enhanced. Adding vitamins D3 and C to the base or primary compositions in combination with a source of ellagic acid can enhance and promote health by improving stem cell circulation and plasticity. By further adding beta glucan, fulvic acid, phycocyanin and phenylethylmanine to the combination of a source of ellagic acid and one or more vitamins, such as vitamin D3 and C, an effective disease fighting and health promoting composition results.

Additional vitamins can add additional health benefits to the base or primary compositions. Additional vitamins include vitamins A, E, K, thiamin, riboflavin, niacin, vitamin B6, folic acid and pantothenic acid.

Minerals such as calcium, iron, phosphorus, iodine, magnesium, zinc, selenium, copper, manganese, chromium and molybdenum can also be combined with any source of ellagic acid and with the base or primary compositions to further promote health. These minerals can also be combined with any source of ellagic acid and any one or more of beta glucan, fulvic acid, phycocyanin, phenylethylamine, and one or more vitamins as described above.

To further promote health and fight disease such as cancer, additional minerals such as one or more of boron selenium, silicon, chloride, sodium, tin, cobalt, titanium, nickel, vanadium, fluoride, potassium and germanium can be combined with a source of ellagic acid or with any of the other combinations described above including the base and primary compositions.

There has been disclosed the best embodiments of the dietary supplement and method of use presently contemplated. Numerous modifications and variations of the supplements are possible in light of the above teachings. It is therefore to be understood that within the scope of the appended claims, this disclosure may be practiced otherwise than as specifically described herein. For example, the base or primary compositions can be enhanced by the addition of any one ingredient or any combination of two, three, four, five or more ingredients noted above. Each ingredient provides an incremental improvement in health and wellness.

What is claimed is:

1. A dietary supplement administered at least once daily for promoting health, body repair and the production of stem cells, comprising:
    about 25 to 175 mg of fulvic acid providing minerals and amino acids;
    about 25 to 175 mg of phycocyanin reducing inflammation;
    about 30 to 220 mg of beta glucan comprising polysaccharides aiding in the transport of said fulvic acid and said phycocyanin from a digestive tract into a bloodstream, said beta glucan also increasing the number of circulating stem cells; and
    about 0.5 to 15 mg of anhydrous trimethylglycine acting as a methyl donor and also increasing absorption of said fulvic acid, said phycocyanin and said beta glucan from a digestive tract into a bloodstream.

2. The dietary supplement of claim 1, further comprising about 6 to 45 mg of phenylethylamine hydrochloride reducing depression and promoting alertness.

3. The dietary supplement of claim 1, wherein said fulvic acid, said phycocyanin said beta glucan and said trimethylglycine are provided in a capsule or tablet.

4. The dietary supplement of claim 1, wherein said fulvic acid, said phycocyanin, said beta glucan and said anhydrous trimethylglycine comprise a single dosage administered orally at least twice daily.

5. The dietary supplement of claim 1 wherein said dietary supplement is provided in a 750 mg or larger tablet or capsule.

6. The dietary supplement of claim 1, further comprising one or more supplements selected from the group consisting of phenylethylamine hydrochloride, curcumin, silymarin, resveratrol, astragalus root extract, astragoloside IV, L-carnosine, vitamin D3 and vitamin C.

7. The dietary supplement of claim 1, wherein said beta glucan comprises 1,3/1,6 glucan.

8. The dietary supplement of claim 1, further comprising a source of ellagic acid.

9. The dietary supplement of claim 8, wherein said source of ellagic acid comprises raspberries.

10. The dietary composition of claim 8, wherein said source of ellagic acid comprises black raspberry powder.

* * * * *